US009162051B2

(12) United States Patent
Morrell

(10) Patent No.: US 9,162,051 B2
(45) Date of Patent: Oct. 20, 2015

(54) TREATMENT OF LANGUAGE, BEHAVIOR AND SOCIAL DISORDERS

(75) Inventor: Martha J. Morrell, Atherton, CA (US)

(73) Assignee: NeuroPace, Inc., Mountain View, CA (US)

(*) Notice: Subject to any disclaimer, the term of this patent is extended or adjusted under 35 U.S.C. 154(b) by 1547 days.

(21) Appl. No.: 11/525,586

(22) Filed: Sep. 21, 2006

(65) Prior Publication Data

US 2008/0077191 A1 Mar. 27, 2008

(51) Int. Cl.
| | |
|---|---|
| *A61N 1/05* | (2006.01) |
| *A61B 5/0476* | (2006.01) |
| *A61B 5/16* | (2006.01) |
| *A61B 5/00* | (2006.01) |
| *A61N 1/36* | (2006.01) |

(52) U.S. Cl.
CPC ............ *A61N 1/0531* (2013.01); *A61B 5/0476* (2013.01); *A61B 5/165* (2013.01); *A61B 5/4094* (2013.01); *A61N 1/0539* (2013.01); *A61N 1/36082* (2013.01)

(58) Field of Classification Search
CPC  A61N 1/3605; A61N 1/36082; A61N 1/3606
USPC .................................................... 607/45, 46
See application file for complete search history.

(56) References Cited

U.S. PATENT DOCUMENTS

| | | | | |
|---|---|---|---|---|
| 5,928,272 | A * | 7/1999 | Adkins et al. ................... | 607/45 |
| 6,006,124 | A | 12/1999 | Fischell et al. | |
| 6,016,449 | A | 1/2000 | Fischell et al. | |
| 6,353,754 | B1 | 3/2002 | Fischell et al. | |
| 6,810,285 | B2 | 10/2004 | Pless et al. | |
| 7,146,217 | B2 * | 12/2006 | Firlik et al. ..................... | 607/45 |
| 2002/0177882 | A1 | 11/2002 | DiLorenzo | |
| 2005/0021104 | A1 * | 1/2005 | DiLorenzo ..................... | 607/45 |
| 2006/0058856 | A1 | 3/2006 | Morrell | |
| 2006/0265022 | A1 * | 11/2006 | John et al. ....................... | 607/45 |
| 2007/0038264 | A1 * | 2/2007 | Jaax et al. ....................... | 607/45 |
| 2007/0055320 | A1 | 3/2007 | Weinand | |
| 2007/0100389 | A1 | 5/2007 | Jaax et al. | |

OTHER PUBLICATIONS

Hrdlicka, M. et al. (2004). "Not EEG Abnormalities but Epilepsy is Associated with Autistic Regression and Mental Functioning in Childhood Autism," *European Child & Adolescent Psychiatry* 13(4):209-213.

(Continued)

*Primary Examiner* — Christopher D Koharski
*Assistant Examiner* — Michael D Abreu
(74) *Attorney, Agent, or Firm* — Arent Fox LLP

(57) ABSTRACT

Methods of treating language, behavioral and social disorders are described, including methods of treating language disorders associated with electrographic abnormalities in the primary or associative language cortex of persons with autism spectrum disorders, pervasive developmental delay or acquired epileptic aphasia. A language, behavioral and social disorder may be treated by detecting epileptiform activity or an electrographic seizure for a subject's brain and applying neurostimulation to a language cortical region of the subject's brain (e.g., a primary or associative language cortical region). Detection of epileptiform activity or an electrographic seizure and stimulation of language cortex may be performed by a sensing and/or stimulation electrode that is inserted into a subject's brain and connected to one or more neurostimulation devices for monitoring and/or stimulating the language cortex.

6 Claims, 9 Drawing Sheets

(56) References Cited

OTHER PUBLICATIONS

Hughes, J. R. et al. (Jan. 2005). "EEG and Seizures in Autistic Children and Adolescents: Further Findings with Therapeutic Implications," *Clinical EEG Neuroscience* 36(1):15-20.

Neville, B. R. G. et al. (Feb. 1997). "Surgical Treatment of Severe Autistic Regression in Childhood Epilepsy," *Pediatric Neurology* 16(2):137-140.

Park, Y. D. (2003). "The Effects of Vagus Nerve Stimulation Therapy on Patients with Intractable Seizures and Either Landau-Kleffner Syndrome or Autism," *Epilepsy & Behavior* 4(3):286-290.

Rossi, P. G. et al. (Mar./Apr. 1995). "EEG Features and Epilepsy in Patients with Autism," *Brain and Development* 17(2):169-174.

Tharp, B. R. (2004). "Epileptic Encephalopathies and Their Relationship to Developmental Disorders: Do Spikes Cause Autism?" *Mental Retardation and Developmental Disabilities Research Reviews* 10:132-134.

Trevathan, E. (Aug. 2004). "Seizures and Epilepsy Among Children with Language Regression and Autistic Spectrum Disorders," *Journal of Child Neurology* 19(S1):S49-57.

Tuchman, R. et al. (Oct. 2002). "Epilepsy in Autism," *The Lancet Neurology* 1:352-358.

Weiland, J. D. et al. (Jul. 2000). "Chronic Neural Stimulation with Thin-Film, Iridium Oxide Electrodes," *IEEE Transactions on Biomedical Engineering* 47(7):911-918.

* cited by examiner

TREATMENT OF LANGUAGE, BEHAVIOR AND SOCIAL DISORDERS

BACKGROUND OF THE INVENTION

Language disorders may have psychological and physiological etiologies. For example, the autism spectrum disorders (autism, pervasive developmental disorder, and acquired epileptic aphasia) are associated with language, behavior and social disability. These disabilities are believed to be a manifestation of electrographic and other functional disturbances in one or more language regions of the brain, as well as regions mediating behavior and social interaction skills. Persons with autism and pervasive developmental disorders, as well as acquired epileptic aphasias such as Landau-Kleffner, have a high prevalence of epilepsy and of epileptiform abnormalities.

Autism (sometimes called "classical autism") is the most common condition in a group of developmental disorders known as the autism spectrum disorders. The Diagnostic and Statistical Manual of Mental Disorders (DSM-IV) defines autistic disorder as a syndrome with qualitative impairments in social interaction, communication, and restricted and stereotyped patterns of behavior, interests and activities. Autism varies widely in its severity and symptoms and may go unrecognized, especially in mildly affected children, or when masked by more debilitating handicaps. Symptoms typically begin before age 3 and may include problems using and understanding language; difficulty relating to people, objects, and events; unusual play with toys and other objects; difficulty with changes in routine or familiar surroundings, and repetitive body movements or behavior patterns.

Other autism spectrum disorders are characterized by delays in the development of socialization and communication skills. Asperger syndrome is an autism spectrum disorder characterized by a greater or lesser degree of impairment in language and communication skills, as well as repetitive or restrictive patterns of thought and behavior. Other autism spectrum disorders include Rett syndrome, childhood disintegrative disorder and pervasive developmental disorder not otherwise specified (usually referred to as PDD-NOS).

Landau-Kleffner syndrome is the best-described syndrome of acquired epileptic aphasia. This condition affects children, usually between the ages of 3 and 7, who previously had no developmental, language, or interactional difficulties. Subject's typically experience a rather abrupt loss of language comprehension and expression, usually coincident with the onset of seizures and a profoundly abnormal sleep EEG. Electrographic status epilepticus (prolonged seizures) in sleep, or continuous spike-wave in slow-wave sleep is typical in acquired epileptic aphasia and in the Landau Kleffner Syndrome (Trevathan E., "Seizures and epilepsy among children with language regression and autistic spectrum disorders." *J Child Neurol* 2004;19(S1):S49-57). The cause for the aphasia in Landau-Kleffner syndrome is uncertain. The seizures and the aphasia are believed to reflect abnormal brain functioning or the aphasia may be a consequence of the seizure discharges.

Clinically evident seizures, as well as subclinical epileptiform discharges and epileptiform electrographic abnormalities, may exacerbate or even cause the cognitive, language and behavior disorders characterizing the autism spectrum disorders and acquired epileptic aphasias. As many as 75% of children with autism have electroencephalogram (EEG) abnormalities and up to 46% have clinical seizures (Hughes J R, Melyn M., "EEG and seizures in autistic children and adolescents: further findings with therapeutic implications." *Clin EEG Neurosci* 2005;36(1):15-20; Hrdlicka M., Komarck V., Propper L., Kulisck R., Zumrova A., Faladova L., Havlociocova M., Sedlacek Z., Blainy M., Urbanek T., "Not EEG abnormalities but epilepsy is associated with autistic regression and mental functioning in childhood autism." *Eur Child Adolesc Psychiatry* 2004;13(4):209-213; Tharp BR, "Epileptic encephalopathies and their relationship to developmental disorders: do spikes cause autism?" *Ment Retard Dev Disabil Res Rev* 2004;10(2):132-134). The prevalence of epilepsy and epileptiform abnormalities in persons with autism spectrum disorders is highest in those with moderate to severe retardation, motor deficits, severe receptive language deficits (Tuchman R., Rapin I., "Epilepsy in autism." *Lancet Neurol* 2002;1 (6):352-358), early language regression (Trevathan E., "Seizures and epilepsy among children with language regression and autistic spectrum disorders." *J Child Neurol* 2004; 19(S1):S49-57) or abnormal development during the first year of life. Epileptic seizures are also associated with progressive regression in children with autism (Rossi P. G., Parmeggiani A., Bach V., Santucci M., Visconti P., "EEG features and epilepsy in patients with autism." *Brain Dev* 1995;17(3):169-174).

Currently, there is no cure for autism spectrum disorders or acquired epileptic aphasias. Therapies and behavioral interventions are designed to remedy specific symptoms. Treatment plans coordinate therapies and interventions that target social interaction, verbal and nonverbal communication, and obsessive or repetitive routines and interests. Medications are used to address specific behavioral problems. Furthermore, we are not aware of any randomized clinical trials of treatments for autistic language regression. Some persons with autism improve cognitively when treated with antiepileptic drugs (AEDs). However, the potential for cognitive side effects limits AED use.

As an alternative or adjunct to medication, surgical interventions have also been used as treatments. For example, vagus nerve stimulation (VNS) and multiple subpial transections, or cortical resection, have been performed to treat autism spectrum disorders. The impact of VNS on quality of life and alertness in 6 children with Landau-Kleffner Syndrome and 59 persons with autism was examined utilizing a retrospective subject outcome registry (Park Y. D., "The effects of vagus nerve stimulation therapy on patients with intractable seizures and either Landau-Kleffner syndrome or autism." *Epilepsy Behav* 2003;4(3):286-290). Fifty-eight percent of the subjects with Landau-Kleffner Syndrome and 78% of the subjects with autism reported improved quality of life and enhanced alertness. It is not possible to differentiate whether these effects were related to reductions in seizures or to an independent mood effect given this study design.

Other surgical treatments include subpial transection. For example, a small number of children with Landau-Kleffner syndrome who have not responded to antiepileptic medications have been treated with subpial transection (Nass R, Neville B. G., Harkness W. F., Cross J. H., Cass H. C., Burch V. C., Lees J. A., Taylor S. C., "Surgical treatment of severe autistic regression in childhood epilepsy." *Pediatr Neurol* 1997; 16(2): 137-140). This procedure severs interneuronal connections perpendicular to the trajectory of the cortical neuron. The procedure is performed in the language area of the frontal lobe coincident with the maximal electroencephalographic abnormalities. The procedure is thought to inhibit the propensity for abnormal electroencephalographic discharges to propagate to adjacent neurons while preserving fiber tracts subserving motor and sensory function.

Thus, there is a need for treatments and systems for treating language, behavioral and/or social disorders, and particularly those related to autism, pervasive developmental disorders, and acquired epileptic aphasias. A system and method of using such a system could benefit individuals with autism spectrum disorders and acquired epileptic aphasias, for which there is no effective treatment.

BRIEF SUMMARY OF THE INVENTION

Described herein are methods of treating language, behavioral and social disorders in a subject in need thereof. For example, methods of treating autism spectrum disorders that have associated language, behavioral and social disorders are described. In general, language, behavioral and/or social disorders may be treated by applying stimulation to a language cortical region (e.g., primary or associative language cortex) in response to epileptiform and other abnormal activity, in subjects in need of treatment. In addition to primary or associative language cortex, other neuronal regions may also be stimulated either simultaneously, or in sequence. Treatment may also include scheduled stimulation applied to a language cortical region (and other regions). Thus language, behavioral and social disorders related to autism spectrum disorders or acquired epileptic aphasias may be treated by any of the responsive, scheduled, or responsive and scheduled stimulation methods described herein. In particular, the methods for treating language disorders described herein may include the steps of detecting epileptiform activity in a subject's brain, and applying neurostimulation to a primary and/or associative language cortical region in response to the epileptiform activity.

Although many of the treatment methods and examples provided herein describe language disorders related to autism spectrum disorders or acquired epileptic aphasias, these methods may be used to treat behavioral or social disorders as well. In some variations, language, behavioral and social disorders may be simultaneously treated. The methods described herein may also be used to specifically treat a behavioral or social disorder. Any appropriate language disorder may be treated by the methods described herein, including language disorders related to autism spectrum disorders or acquired epileptic aphasias.

In many of the methods described herein, language disorders may be treated using a device that provides responsive and/or programmed electrical stimulation to a subject's nervous system, particularly neurological regions such as a primary or associative language cortex, the cingulate cortex, frontal cortical regions and other relevant portions of the brain and peripheral nervous system. In particular, language, behavioral and social disorders may be treated by applying neurostimulation to one or more regions of the cerebral cortex mediating behavior and social interactions (e.g., cingulate, prefrontal, insula, or temporal cortex). One device described herein provides continuous monitoring of electrocorticographic signals. Monitoring may take place through electrodes implanted into the brain (e.g., within specific brain regions). Monitoring can identify disturbances in brain electrical activity (e.g., epeliptiform activity), which can direct therapy for those subjects with abnormal electrocorticograms. Since electrographic disturbances are likely to be dynamic, continuous monitoring may aid in timely and accurate intervention.

As described in more detail below, any appropriate brain region my be stimulated, particularly primary or associative language cortex, e.g., Broca's area, Wemicke's area, the superior temporal sulcus, Heschl's gyrus, planum polare, planum temporale, and/or the anterior superior insular cortices.

Responsive and/or scheduled stimulation of a subject's nervous system (which may be referred to as "neurostimulation") may be applied to more than one region of a subject's brain in addition to a language cortex region. For example, stimulation may be applied to the cingulate cortex, prefrontal, insula, temporal cortex, or other regions of the cerebral cortex in response to abnormal electrographic activity (and/or at a prescheduled time). In addition to treating language disorders, the treatment methods described herein may improve social and emotional disability in a subject, including subjects having autism spectrum disorders or acquired epileptic aphasias.

In some variations, the step of applying neurostimulation comprises applying neurostimulation to a language area of the frontal lobe. Applying neurostimulation may involve applying neurostimulation to all or a part of the primary or associative language cortical region of the brain coincident with the epileptiform activity or electrographic seizure. Detecting epileptiform activity or an electrographic seizure may comprise detecting the activity from at least one electrode implanted in the brain. As described in more detail below, epileptiform activity may be identified based on any appropriate characteristic. For example, when the activity is monitored by electrodes sensitive to neural electrical activity, epileptiform activity or an electrographic seizure may be identified by comparison with background electrographic activity or based on characteristics of epileptiform activity and electrographic seizures.

Any appropriate stimulation may be applied to treat a language, behavioral and/or social disorder, particularly electrical stimulation. For example, appropriate stimulation may comprise biphasic charged-balanced pulses of 100 to 200 Hz frequency, 100-200 msec duration, pulse width of 100 µsec, and appropriate current necessary to achieve a charge density of 6 $\mu C/cm^2$ per phase. Different or variable stimulation may be used, e.g., depending on the response of the abnormal electrographic activity. Stimulation can be adjusted to achieve the desired response as follows: pulse width can be set between 40 to 1000 microseconds, pulse frequency may be, for example, between 1 to 333 Hz and current can be adjusted between 0.5 and 12 milliamps. The neurostimulation may be applied by one or more electrodes. In some variations, when one or more electrodes are used to detect epileptiform activity, the same electrode used to detect the epileptiform activity is also used to apply neurostimulation. The neurostimulation applied may further depend on the location of the electrodes (e.g., the brain region), the level of activity, the time of day, the arousal state (e.g., asleep/awake status) of the subject, etc. The stimulation may be modified to help the subject receive optimal stimulation with minimal adverse effects. It is reasonable to assume that individual subjects will differ in terms of the optimal stimulus settings. Thus, the stimulation may be tailored to individual subjects, or it may be based on characteristics taken from a population of subjects. In some variations, the stimulation is the same for any subject. "Stimulation" is not limited to excitatory stimulation, but includes inhibitory stimulation as well.

As mentioned above, one or more electrodes may be used to detect and/or measure epileptiform activity or an electrographic seizure, and/or to apply neurostimulation. In some variations, the electrode or electrodes are implanted in the appropriate brain regions. For example, the electrodes may be implanted in the cortex, or adjacent to the region of interest, such as a primary or associative language region. Implanted electrodes (e.g., electrodes implanted into the subject's brain) may refer to electrodes that abut the region of interest (e.g., cortex) and/or electrodes that are inserted into the brain tissue. In some variations, detecting epileptiform activity or an electrographic seizure in a subject comprises measuring the subject's EEG. Electrodes implanted in the subject's brain may be used. Electrodes external to the subject's brain may also be used. In some variations, scalp electrodes may be used in addition to (or instead of) implanted brain electrodes.

As mentioned, a method of treating a language disorder may also involve applying neurostimulation to a second brain region in response to epileptiform activity or an electrographic seizure. For example, neurostimulation may be applied to a second cortical region (e.g., the cingulate gyrus), in addition to a primary or associative language region.

A language, behavior or social disorder may also be treated by applying neurostimulation at scheduled intervals to a cortical region mediating language, behavior, or social interaction. Stimulation can be continuous, or applied for a set duration and with a set inter-stimulus interval. In some variations, the method for treating a language disorder involves applying stimulation both in response to epileptiform activity or an electrographic seizure, as well as at scheduled intervals. Scheduled intervals may be regularly scheduled (e.g., so that neurostimulation can occur at pre-set times), or may be scheduled to occur based on a subject's activity (e.g., when the subject is sleeping, etc.). Thus, in some variations, a neurostimulation may be scheduled to be applied while the subject is sleeping.

Also described herein are methods of treating autism-related language, behavioral or social disorders in a subject in need thereof. These methods include the steps of receiving electrical signals corresponding to a subject's neural (e.g., brain) electrical activity, detecting epileptiform activity or an electrographic seizure from the received electrical signals, and applying neurostimulation to a primary or associative language cortical region of the subject's frontal lobe in response to the epileptiform activity or an electrographic seizure. The step of receiving electrical signals corresponding to electrical activity of a subject's brain may include receiving electrical activity from electrodes implanted in the subject's brain.

A neurostimulation device may be implanted so that at least a portion of the device is attached to the subject's cranium and includes one or more leads having electrodes at the distal end of each lead. The electrodes can be placed within or against relevant regions of the brain in the form of a depth electrode or a subdural electrode. A single electrode or multiple electrodes may be implanted. The device typically monitors brain activity, and may be configured to monitor electrical activity, changes in concentration of inhibitory or excitatory neurochemicals, changes in proteins or other gene products, or changes in temperature or markers of metabolic rate. Sensing electrodes are typically placed over the cortical region of interest.

Optimal stimulation electrodes can be configured over time, as the subject's symptoms and the effects of stimulation are observed. Stimulation may be quite focal, using adjacent electrodes as anode and cathode, or can be applied to multiple regions simultaneously by utilizing all of the electrodes of the device. Also, the electrodes over which neurostimulation is applied can be adjusted according to the subject's short- and long-term response.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

Described here are methods of treating language, behavioral and social disorders. In particular, methods of treating language disorders related to autism spectrum disorders or acquired epileptic aphasias are descried. As mentioned previously, many of the treatment methods provided herein may be used specifically to treat language disorders. Behavioral or social disorders may also be treated by the methods described herein. In some variations, the methods described herein may be used to treat a behavioral or social disorder, regardless of the presence of a language disorder. As used herein, language disorders may include language disorders related to autism spectrum disorders or acquired epileptic aphasias.

Figure 1:
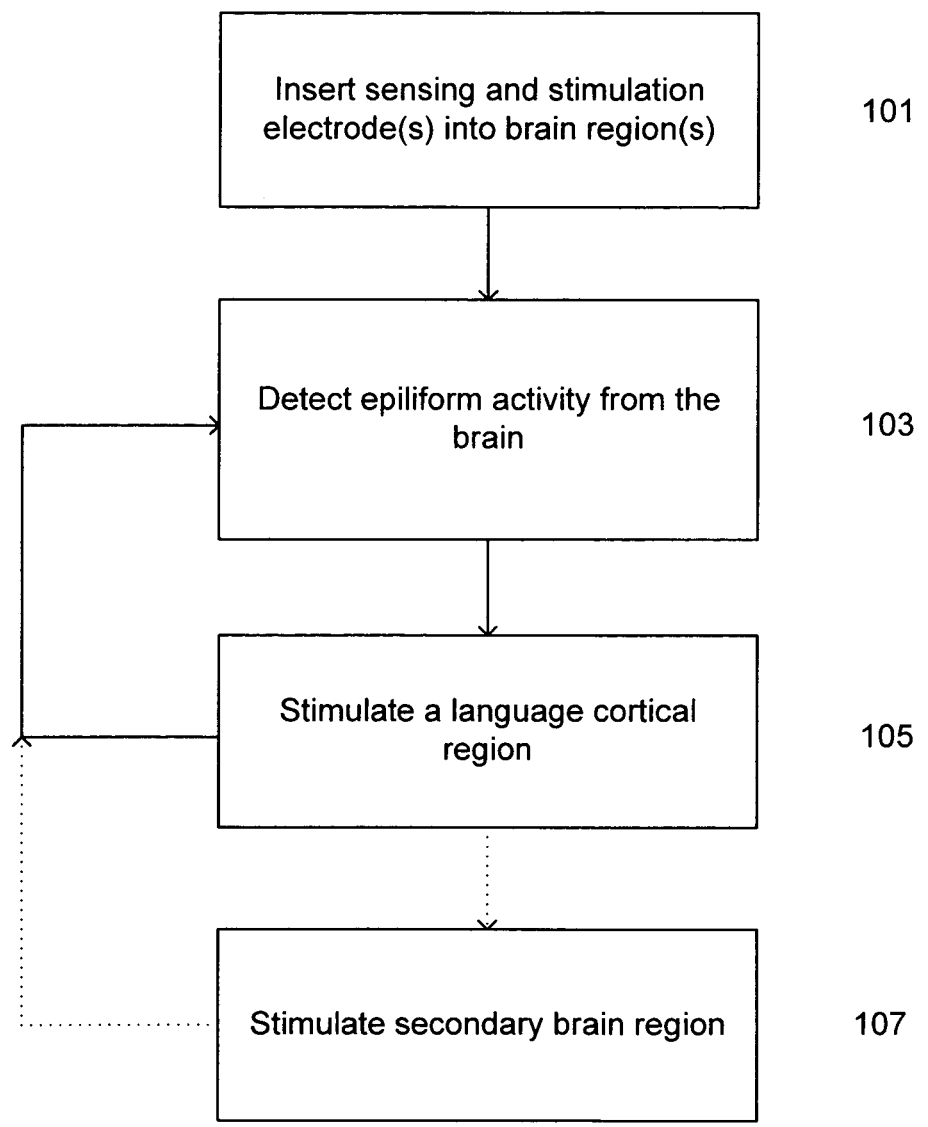
FIG. 1 is a block diagram illustrating one method for treating language, behavioral or social disorders as described herein.

In general, a language, behavioral or social disorder may be treated by detecting epileptiform activity or an electrographic seizure from the brain 103, and applying neurostimulation to a primary or associative language cortical region 102 of the brain, as illustrated schematically in FIG. 1. In the embodiment of the method shown in FIG. 1, a sensing and/or stimulation electrode is inserted into a subject's brain. The sensing and/or stimulating electrodes are connected to one or more devices for monitoring and/or stimulating the brain (e.g., language cortex), referred to as neurostimulation devices. Examples and illustrations of the kinds of sensing and/or stimulation devices that may be used to treat language disorders are described in more detail below. Generally, these devices are configured to both detect epileptiform activity and/or an electrographic seizure in a subject's brain and apply neurostimulation. However, in some variations, separate devices are used for monitoring brain activity and applying neurostimulation.

Brain activity is monitored 103 so that epileptiform activity or an electrographic seizure (actual activity or predicted epileptiform activity or an electrographic seizure) can be detected. Activity may be detected by comparing ongoing activity to typical epileptiform activity, including identifying characteristics of epileptiform activity or an electrographic seizure from ongoing brain activity. This is described in greater detail below. Once epileptiform activity or an electrographic seizure is detected, the subject's language cortex is stimulated 105. In some variations, stimulation is provided at the location at or near the focal brain region where the activity was detected. Appropriate stimulation is also described more fully below. Additional stimulation to secondary brain regions may be applied 107. For example, a secondary brain region (e.g., cingulate gyrus) may also be simulated when (or before or after) the primary or associative language cortex is stimulated.

The methods for treating language, behavioral or social disorders described herein may be used on any appropriate subject, particularly subjects in need of treatment of a language disorder. For example, subjects (who may also be referred to as "patients") may have autism, pervasive developmental disorders, and/or acquired epileptic aphasias. Examples and illustrations of the steps for treating subjects having these disorders are provided below, including exemplary devices and systems that may be used as part of the treatment.

A. Insertion of a Sensing and/or Stimulation Device

Electrodes for sensing epileptiform activity or an electrographic seizure may be implanted into a subject's brain and connected to a neurostimulation device. Alternatively, electrodes may be attached to the subject's head so that they detect activity through the skull and any intervening tissues. In some variations, the neurostimulation device to which electrodes are connected is affixed to the subject's skull. The electrodes may be configured as probes that are used to detect activity. Electrodes may be part of one or more electrical leads that connects either directly or indirectly (e.g., wirelessly) to a neurostimulation device. In some variations, the same electrodes may be used both to sense activity and to apply neurostimulation.

Figure 3:
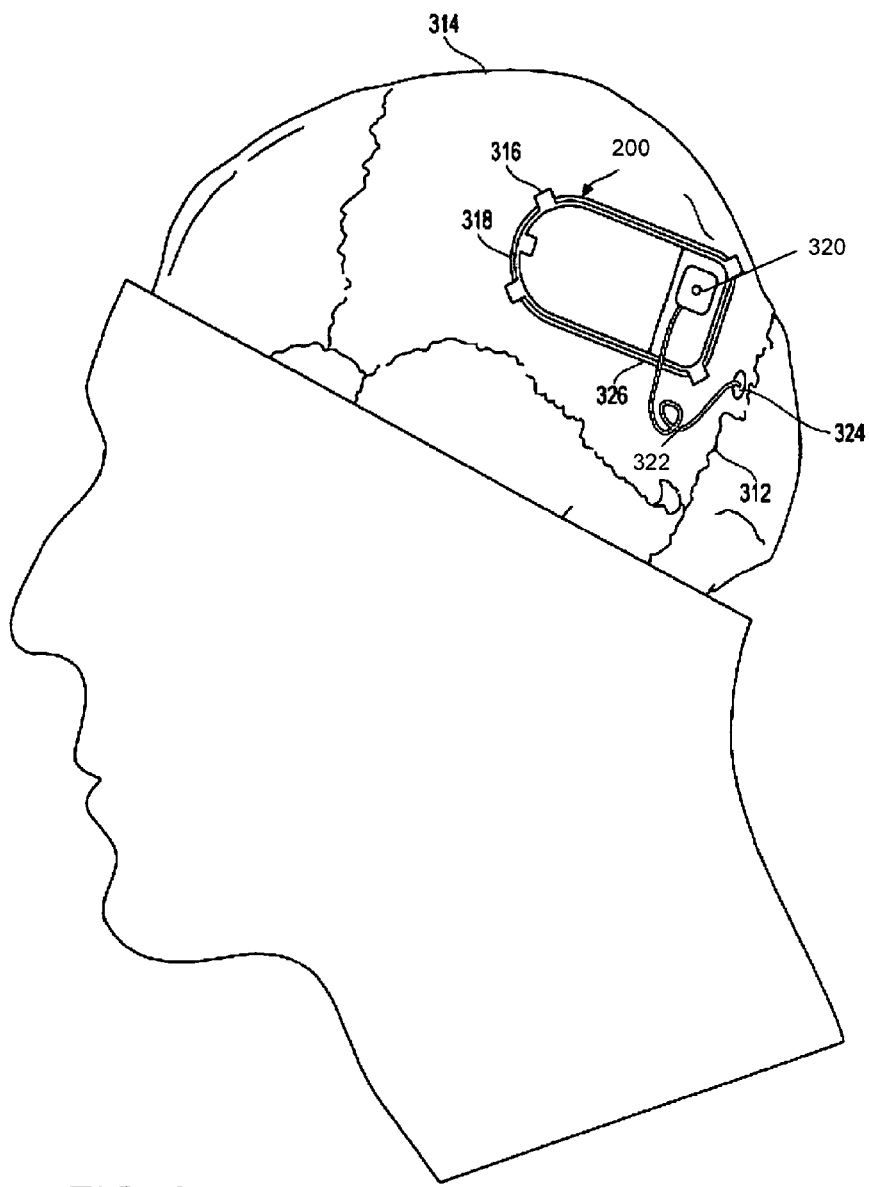
FIG. 3 is a schematic illustration of a subject's cranium showing the implantable neurostimulation device of FIG. 2 as implanted, including a lead extending to the subject's brain.
Figure 4:
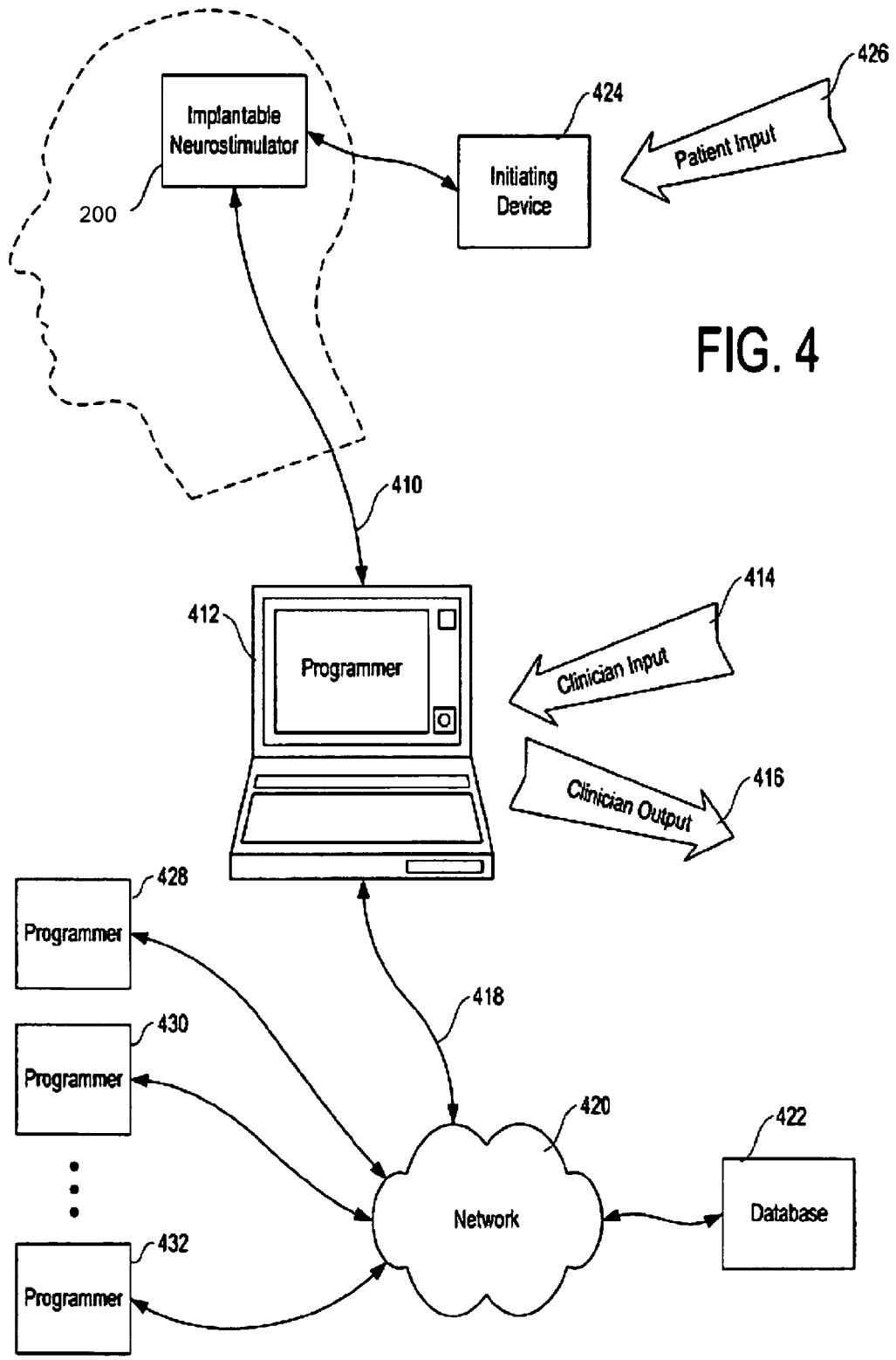
FIG. 4 is a block diagram illustrating the operation of a neurostimulation device.
Figure 5:
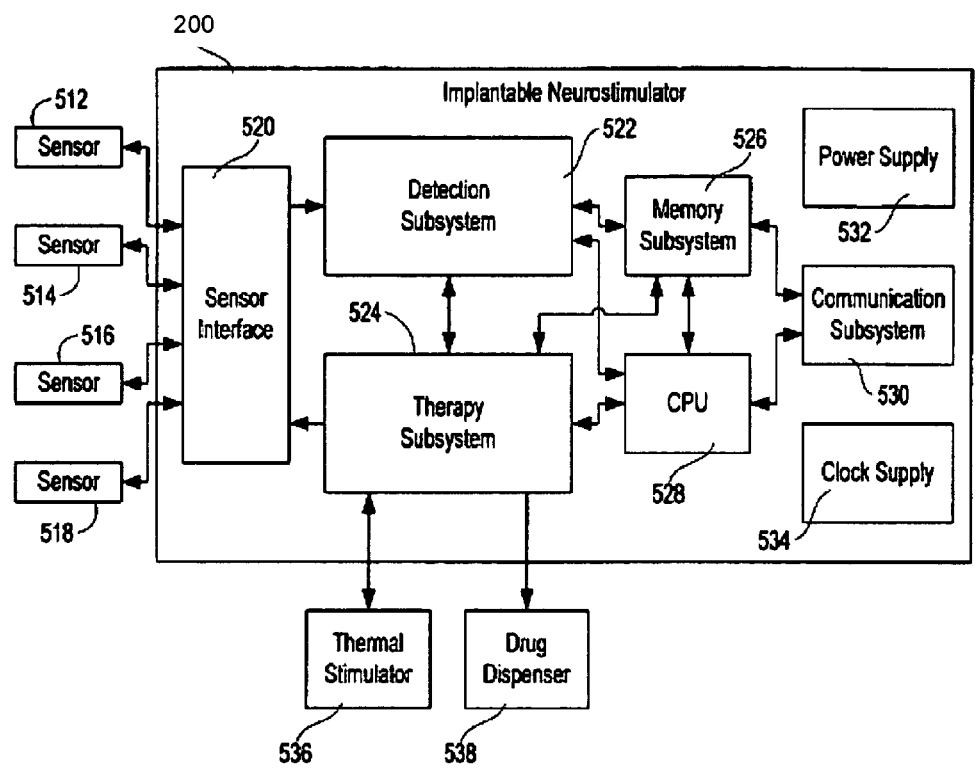
FIG. 5 is a block diagram illustrating subsystems of a neurostimulation device.

One example of a device (e.g., a "neurostimulation device") for sensing epileptiform activity or an electrographic seizure and applying neurostimulation to a language region of the brain is shown schematically in FIG. 5, and illustrated in FIGS. 2A-4. This device is similar to the devices illustrated in U.S. Patent Application Publication No. 2006/0058856, and U.S. Pat. No. 6,810,285, both of which are incorporated herein by reference in the entirety. It will be apparent that devices or systems for sensing epileptiform activity or an electrographic seizure and for applying neurostimulation may be embodied in a wide variety of forms. Consequently, the specific structural and functional details disclosed herein are representative and do not limit the scope of the invention.

Figure 2A:
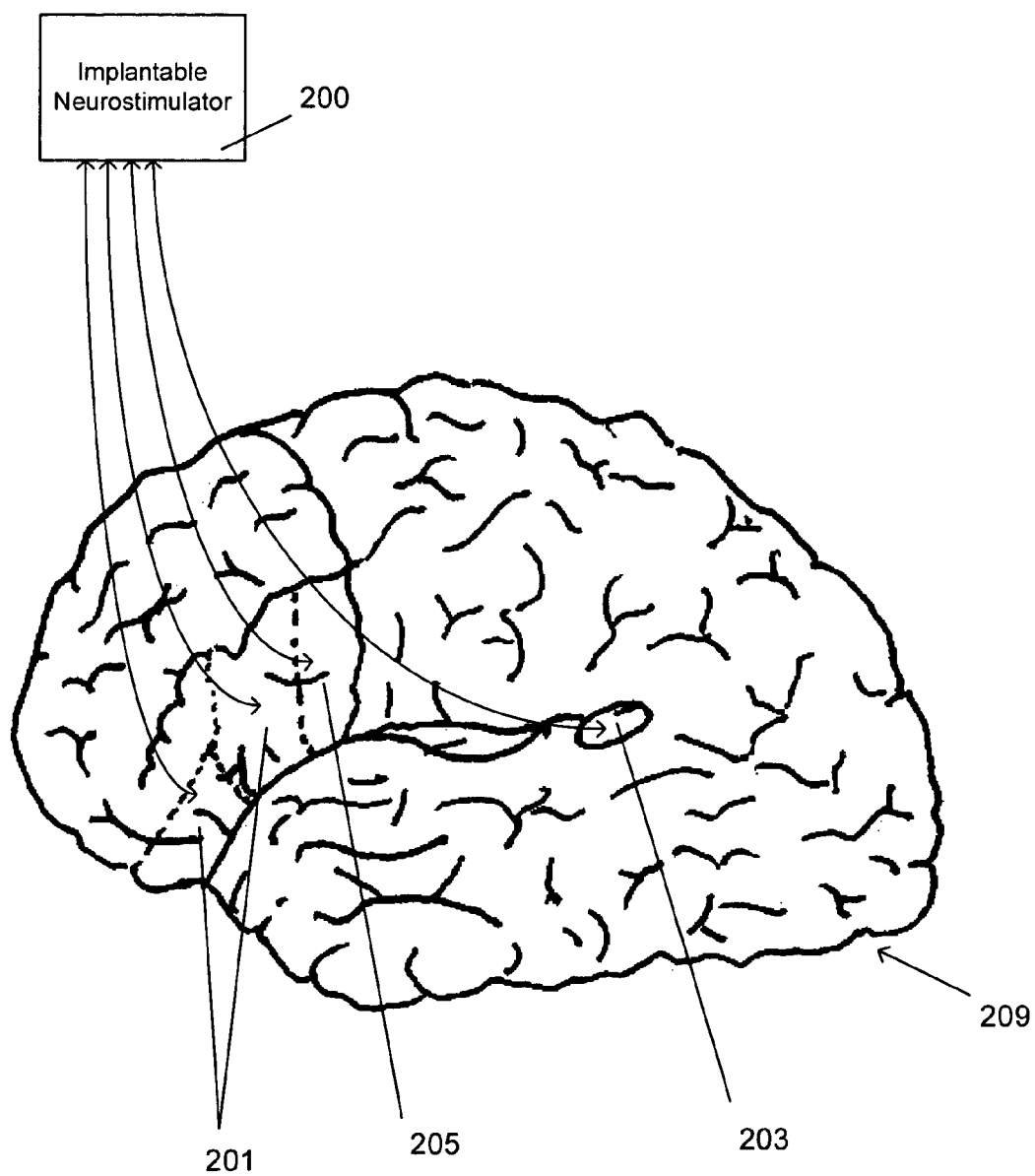
FIG. 2A is a schematic illustration of an implantable neurostimulation device contacting various language cortical regions of a brain.

FIG. 2A illustrates, schematically, an implantable neurostimulation device 200 that is in communication with various regions of a subject's brain 201, 203, 205, particularly cortical language regions. FIG. 2 shows a lateral surface of the cerebral hemisphere, including regions identified as important in language processing, formation and interpretation, such as the opercular 205 and triangular gyri 201 (e.g., Broca's area), and Wernicke's area 203. The variation of the neurostimulation device shown in this figure may receive signals from the subject's brain 209 and can respond by applying stimulation to the brain regions (e.g., language cortical regions) where probes have been inserted.

Figure 2B:
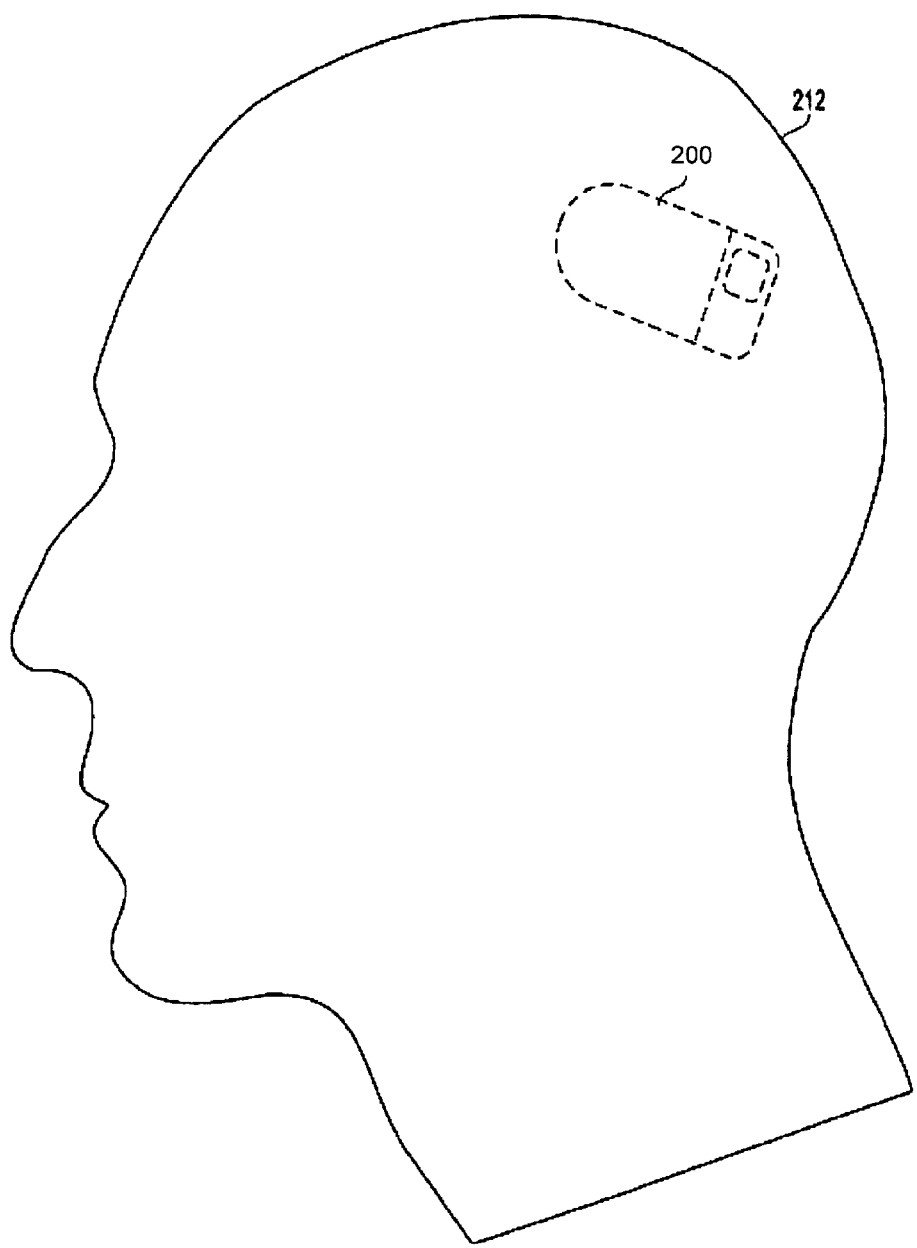
FIG. 2B shows a schematic illustration of a subject's head showing placement of an implantable neutostimualtor.

FIG. 2B depicts an intracranial implantation of a neurostimulation device 200 according to the invention, which in one embodiment is a small self-contained responsive neurostimulator. As mentioned, a neurostimulation device (including a responsive neurostimulation device) may detect or predict neurological events, such as epileptiform electrical activity, and may provide stimulation (e.g., electrical stimulation) to neural tissue in response to that activity, where the stimulation is specifically intended to treat a language disorder. For example, stimulation may be provided to terminate the epileptiform activity or an electrographic seizure, to prevent epileptiform activity, or to prevent or lessen the effects or severity of language disorders associated with (or caused by) epileptiform activity or an electrographic seizure. The neurostimulation device may detect epileptiform activity or an electrographic seizure by any appropriate method.

A neurostimulation device may be capable of detecting or predicting epileptiform neurological events, as described more fully below. Preferably, neurological events representing epileptiform activity or an electrographic seizure can be detected when they are actually occurring, in an onset stage, or as a predictive precursor before clinical symptoms begin. The device may also be configured to detect and/or respond to other types of neurological activity, such as activity associated with movement disorders (e.g. the tremors characterizing Parkinson's disease), migraine headaches, and chronic pain.

A neurostimulation device such as the device shown schematically in FIGS. 2A and 2B may be implanted intracranially in a subject's parietal bone 310, in a location anterior to the lambdoid suture 312 (see FIG. 3). It should be noted, however, that the placement described and illustrated herein is merely exemplary, and other locations and configurations are also possible, in the cranium or elsewhere, depending on the size and shape of the device and individual subject needs, or other factors. The device 200 is preferably configured to fit the contours of the subject's cranium 314. In an alternative embodiment, the device 200 is implanted under the subject's scalp 212, but external to the cranium. In yet another alternative embodiment, when it is not possible to implant the device intracranially, it may be implanted pectorally (not shown), with leads extending through the subject's neck and between the subject's cranium and scalp, as necessary.

It should be recognized that the embodiment of the device 200 described and illustrated herein is preferably a neurostimulation device for detecting and treating language disorders (and related disorders) by detecting epileptiform activity or an electrographic seizure (or its onset or precursor activity) and applying neurostimulation to the appropriate brain region(s), thereby alleviating the disorder(s). Although the applicant believes that the stimulation of one or more language areas of the brain before or during epileptiform activity or an electrographic seizure may help treat language, behavioral or social disorders, the methods and systems described herein should not be limited to any particular theory of operation.

The neurostimulation device 200 may be any appropriate device capable of detecting neurological conditions and events (e.g., epileptiform activity or an electrographic seizure) and performing actions in response thereto. The actions performed by the device 200 need not be therapeutic, but may involve data recording or transmission, providing warnings to the subject, or any of a number of known alternative actions. A neurostimulator may not be a single device, but may be a system of component devices. For example, a detection device may signal to a separate stimulation device. Thus, a neurostimulation device may also act as a diagnostic device, and may be interfaced with external equipment, as will be discussed in further detail below.

The intracranially implanted device 200 shown in FIG. 3 is affixed in the subject's cranium 314 by way of a ferrule 316. The ferrule 316 is a structural member adapted to fit into a cranial opening, attach to the cranium 314, and retain the device 200. In one variation, the device 200 is implanted by performing a craniotomy in the parietal bone 310 anterior to the lambdoid suture 312 to define an opening 318 slightly larger than the device 200. The ferrule 316 is inserted into the opening 318 and affixed to the cranium 414, ensuring a tight and secure fit. The device 310 is then inserted into and affixed to the ferrule 316.

As shown in FIG. 3, the device 200 includes a lead connector 320 adapted to receive one or more electrical leads, such as a first lead 322. The lead connector 320 acts to physically secure the lead 322 to the device 200, and facilitates electrical connection between a conductor in the lead 322 coupling an electrode with circuitry within the device 200. The lead connector 320 accomplishes this in a substantially fluid-tight environment with biocompatible materials.

A lead, including the lead 322 as illustrated in FIG. 3, is typically a flexible, elongated member having one or more conductors. As shown, the lead 322 is coupled to the device 200 via the lead connector 320, and is generally situated on the outer surface of the cranium 314 (and under the subject's scalp 212), extending between the device 200 and a burr hole 324 or other cranial opening, where the lead 322 enters the cranium 314 and is coupled to a depth electrode (e.g., one of the sensors 512-518 of FIG. 5) implanted in a desired location in the subject's brain. If the length of the lead 322 is substantially greater than the distance between the device 200 and the burr hole 324, any excess may be urged into a coil configuration under the scalp. As described in U.S. Pat. No. 6,006,124 to Fischell, et al., which is hereby incorporated by reference as though set forth in full herein, the burr hole 324 is sealed after implantation to prevent further movement of the lead 322; in an embodiment of the invention, a burr hole cover apparatus is affixed to the cranium 314 at least partially within the burr hole 324 to provide this functionality.

The device 200 includes a durable outer housing 326 fabricated from a biocompatible material. Titanium, which is light, extremely strong, and biocompatible, is used in analogous devices, such as cardiac pacemakers, and may serve advantageously in this context as well. As the device 200 is self-contained, the housing 326 encloses a battery and any electronic circuitry necessary or desirable to provide the functionality described herein, as well as any other features. A telemetry coil may be in the interior of the device 200 or provided outside of the housing 326 (and potentially integrated with the lead connector 320) to facilitate communication between the device 200 and external devices.

The neurostimulation device configuration described herein and illustrated in FIG. 3 is self-contained, and may substantially decrease the need for access to the device 200, allowing the subject to participate in normal life activities. Its small size and intracranial placement causes a minimum of cosmetic disfigurement. The device 200 will fit in an opening in the subject's cranium, under the subject's scalp, with little noticeable protrusion or bulge. The ferrule 316 used for implantation allows the craniotomy to be performed and fit verified without the possibility of breaking the device 200, and also provides protection against the device 200 being pushed into the brain under external pressure or impact. A further advantage is that the ferrule 316 receives any cranial bone growth, so at explant, the device 200 can be replaced without removing any bone screws—only the fasteners retaining the device 200 in the ferrule 316 need be manipulated.

FIG. 5 shows a block diagram illustrating functional subsystems of an exemplary neurostimulation device. The implantable neurostimulation device 200 contains a memory subsystem 526 and a CPU 528, which can take the form of a microcontroller. The memory subsystem is coupled to the detection subsystem 522 (e.g., for receiving and storing data representative of sensed EEG or other signals and evoked responses), the therapy subsystem 524 (e.g., for providing stimulation waveform parameters to the therapy subsystem for electrical stimulation), and the CPU 528, which can control the operation of (and store and retrieve data from) the memory subsystem 526. In addition to the memory subsystem 526, the CPU 528 is also connected to the detection subsystem 522 and the therapy subsystem 524 for direct control of those subsystems.

The device 200 may also include a communication subsystem 530, that may be coupled to the memory subsystem 526 and the CPU 528. The communication subsystem 530 enables communication between the device 200 and the external environment, particularly an external programmer 412 and a subject initiating device 424, both of which are described with reference to FIG. 4. FIG. 4 illustrates a system for controlling the neurostimulation device that may be used to treat language disorders. The communication subsystem 530 includes a telemetry coil (which may be situated inside or outside of the housing of an implantable neurostimulation device 200) enabling transmission and reception of signals, to or from an external apparatus, via inductive coupling. Alternative embodiments of the communication subsystem 530 could use an antenna for an RF link or an audio transducer for an audio link. Preferably, the communication subsystem 530 also includes a GMR (giant magnetoresistive effect) sensor to enable receiving simple signals (namely the placement and removal of a magnet) from a subject initiating device; this capability can be used to initiate signal recording.

Several support components may also be present in the neurostimulation device 200, including a power supply 532 and a clock supply 534. The power supply 532 supplies the voltages and currents necessary for each of the other subsystems. The clock supply 534 supplies substantially all of the other subsystems with any clock and timing signals necessary for their operation, including a real-time clock signal to coordinate programmed and scheduled actions and the timer functionality used by the detection subsystem 522.

In some variations of the invention the therapy subsystem 524 is coupled to a thermal stimulator 536 and a drug dispenser 538, thereby enabling therapy modalities other than electrical stimulation. The device may therefore include a stimulation output that may be a stimulation electrode (which may be the same as a recording electrode), a drug dispenser outlet, or a thermal stimulation site (e.g., Peltier junction or thermocouple), etc.

It should be observed that while the memory subsystem 526 is illustrated in FIG. 5 as a separate functional subsystem, the other subsystems may also require various amounts of memory to perform the functions described above and others. Furthermore, while the neurostimulation device 200 is preferably a single physical unit (i.e., a control module) contained within a single implantable physical enclosure, namely the housing described above, other embodiments of the invention might be configured differently. The neurostimulation device 200 may be provided as an external unit not adapted for implantation, or it may comprise a plurality of spatially separate units each performing a subset of the capabilities described above, some or all of which might be external devices not suitable for implantation. Also, it should be noted that the various functions and capabilities of the subsystems described herein may be performed by electronic hardware, computer software (or firmware), or a combination thereof. The division of work between the CPU 528 and the other functional subsystems may also vary—the functional distinctions illustrated in FIG. 5 may not reflect the partitioning and integration of functions in all systems or methods according to the invention.

The neurostimulation device 200 shown in FIGS. 4 and 5 may be used for measurement, detection and treatment. The device 200 is capable of being coupled to a plurality of sensors 512, 514, 516, and 518 (each of which may be individually or together connected to the neurostimulation device 200 via one or more leads), which are shown as electrodes that may be used for both sensing and stimulation as well as the delivery of other treatment modalities. In the illustrated embodiment, the coupling is accomplished through a lead connector. Although four sensors are shown in FIG. 5, it should be recognized that any number is possible, and in the embodiment described in detail below, eight electrodes are used as sensors. In fact, it is possible to employ an embodiment of the invention that uses a single lead with at least two electrodes, or two leads each with a single electrode (or with a second electrode provided by a conductive exterior portion of the housing), although bipolar sensing between two closely spaced electrodes on a lead is preferred to minimize common mode signals including noise.

In one variation, the neurostimulation device 200 is capable of receiving two leads, each with four electrodes. One cortical lead and one depth lead, two cortical leads, or two depth leads can be used simultaneously to achieve the desired coverage of language cortex and other regions, (e.g., cingulate gyrus or other desired brain areas). It will be recognized that other embodiments of a system according to the invention may receive more leads, or leads and sensors in different forms than those specifically disclosed herein. As mentioned above, a lead may have one or more electrodes.

The sensors 512-518 are in contact with the subject's brain (e.g., in contact with a language region of the subject's brain), or are otherwise advantageously located to receive EEG signals or provide electrical stimulation or another therapeutic modality. Each of the sensors 512-518 is also electrically coupled to a sensor interface 520. Preferably, the electrode interface is capable of selecting each electrode as required for sensing and stimulation; accordingly the electrode interface is coupled to a detection subsystem 522 and a therapy subsystem 524 (which may provide electrical stimulation and other therapies). The sensor interface 520 may also provide any other features, capabilities, or aspects, including but not limited to amplification, isolation, and charge-balancing functions, that are required for a proper interface with neurological tissue and not provided by any other subsystem of the device 200.

Once a neurostimulation device has been attached to electrodes implanted into the subject's brain (particularly language cortex), a language disorder may be treated by monitoring brain activity to detect epileptiform activity or an electrographic seizure. As mentioned herein, a neurostimulation device may be an integrated device, so that that the electrodes do not need to be separately attached.

B. Detection of Epileptiform Activity or an Electrographic Seizure

In general, epileptiform activity or electrographic seizures may be detected by monitoring electrical activity of the subject's brain. In one variation, electrographic signals are received by electrodes and analyzed. Epileptiform activity or an electrographic seizure may be recognized by comparing received signals, or characteristics derived from received signals, with signals or characteristics correlated to epileptiform activity or an electrographic seizure. The signals and characteristics correlated with epileptiform activity or an electrographic seizure may be derived from population data, or based on activity or characteristics derived from the specific subject into whom the neurostimulation device has been implanted. Furthermore, the detection of epileptiform activity or electrographic seizures may be modifiable (e.g., learned).

For example, the detection subsystem 522 of the device 200 may include an EEG waveform analyzer. Detection is generally accomplished in conjunction with a central processing unit (CPU) 528. The waveform analyzer is adapted to receive signals from the sensors 512-518 (e.g., electrodes), through the sensor interface (i.e., lead connector) 520, and to process those EEG signals to identify epileptiform activity or an electrographic seizure. One way to implement such EEG analysis functionality is disclosed in detail in U.S. Pat. No. 6,016,449 to Fischell et al., incorporated by reference above. Additional methods are described in U.S. Pat. No. 6,810,285, relevant details of which will be set forth below (and which is also hereby incorporated by reference as though set forth in full). The detection subsystem may optionally also contain further sensing and detection capabilities, including but not limited to parameters derived from other physiological conditions (such as electrophysiological parameters, temperature, blood pressure, neurochemical concentration, etc.). In general, prior to analysis, the detection subsystem performs amplification, analog to digital conversion, and multiplexing functions on the signals in the sensing channels received from the sensors 512-518.

A neurostimulation device may monitor brain activity and detect epileptiform activity or electrographic seizures (or the onset of epileptiform activity or an electrographic seizure) in any appropriate manner. For example, an implantable neurostimulation device may employ a combination of signal processing and analysis modalities, and may reduce data by extracting characteristics or features from the monitored brain activity. For example, a neurostimulation device may extract features such as: line length function (representing sample to sample amplitude variability of an EEG signal within a time window), area function (representing the total deviation of the EEG signal from non-zero over a time window), half waves (representing the interval between a local waveform minimum and a local waveform maximum), and the like. Extracted features may be compared to features that may indicate (individually or in the aggregate) epileptiform activity or an electrographic seizure. For example, line length functions, area functions and/or half waves may fall within a range suggestive or indicative of epileptiform activity or an electrographic seizure. Additional features or characteristics of epileptiform activity or an electrographic seizure may be extracted as well. As mentioned above, these ranges may be preset or modifiable, and may be tailored to a specific subject. Thus, there may be a period of "learning" to determine characteristics correlated to epileptiform activity or an electrographic seizure. In some variations, the range of features may be learned, or additional features may be added to the neurostimulation device.

Epileptiform activity is distinguished from a patient's typical electrographic background by virtue of its sudden onset, morphology, frequency and amplitude. A typical epileptiform discharge is a spike wave. A spike is a sharply contoured wave, typically of less than 200 msec duration. Other common epileptiform discharges are sharp waves, and polyspike waves. Electrographic seizures (which may or may not be accompanied by neurological changes) arise from the background electrographic activity, and are usually characterized by abnormally organized activity which evolves spatially and over time. The waveforms may be spike or sharp waves, or may be rhythmic and high amplitude delta waves (1 to 4 Hz) or even very low amplitude waves of frequencies in excess of 20 to 25 Hz. A physician trained in electroencephalography is able to identify both epileptiform activity and electrographic seizures.

For example, U.S. Pat. No. 6,353,754 (herein incorporated by reference in its entirety) also provides an example of how epileptiform activity may be recognized in an individual subject by developing an optimized set of subject-specific parameters. Brain activity may be recorded over a period of time in which epileptiform activity or an electrographic seizure occurs, and recordings of the activity during epileptic activity may be marked. Computer analysis of this activity can determine waveforms that are characteristic of epileptic activity specific for the individual subject. By comparing ongoing brain activity measured using the same device, epileptiform activity or an electrographic seizure can be detected, and therefore used in the treatments described herein.

Figure 6:
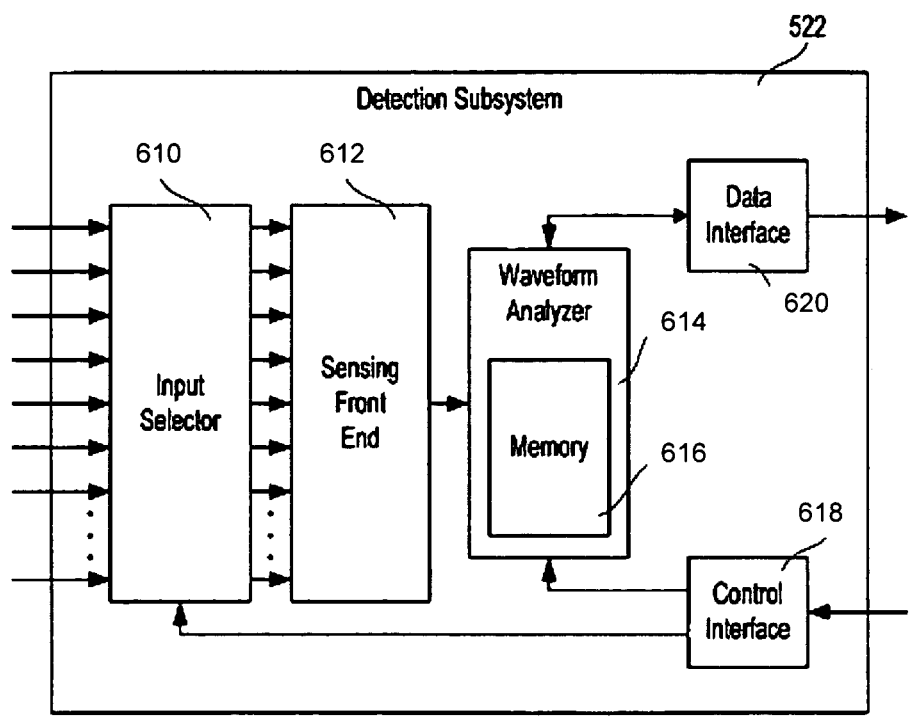
FIG. 6 is a block diagram illustrating components of a detection subsystem of a neurostimulation device as shown in FIG. 5.

FIG. 6 illustrates details of a detection subsystem 522 such as the subsystem shown in FIG. 5. Inputs from the electrodes (sensors 512-518) are on the left, and connections to other subsystems are on the right. Signals received from the sensors 512-518 (as routed through the sensor interface 520) are received in an input selector 610. The input selector 610 allows the device to select which electrodes or other sensors (of the sensors 512-518) should be routed to which individual sensing channels of the detection subsystem 522, based on commands received through a control interface 618 from the memory subsystem 526 or the CPU 528 (FIG. 5). Preferably, when electrodes are used for sensing, each sensing channel of the detection subsystem 522 receives a bipolar signal representative of the difference in electrical potential between two selectable electrodes. Accordingly, the input selector 610 provides signals corresponding to each pair of selected electrodes to a sensing front end 612, which performs amplification, analog to digital conversion, and multiplexing functions on the signals in the sensing channels.

A multiplexed input signal representative of all active sensing channels is then fed from the sensing front end 612 to a waveform analyzer 614. The waveform analyzer 614 is preferably a special-purpose digital signal processor (DSP) adapted for use with the invention, or in an alternative embodiment, may comprise a programmable general-purpose DSP. In the disclosed embodiment, the waveform analyzer has its own scratchpad memory area 616 used for local storage of data and program variables when the signal processing is being performed. In either case, the signal processor performs suitable measurement and detection methods described generally above and in greater detail below. Any results from such methods, as well as any digitized signals intended for storage transmission to external equipment, are passed to various other subsystems of the device 200, including the memory subsystem 526 and the CPU 528 (FIG. 5) through a data interface 620. Similarly, the control interface 618 allows the waveform analyzer 614 and the input selector 610 to be in communication with the CPU 528. The waveform analyzer 614 is illustrated in detail in FIG. 7.

Figure 7:
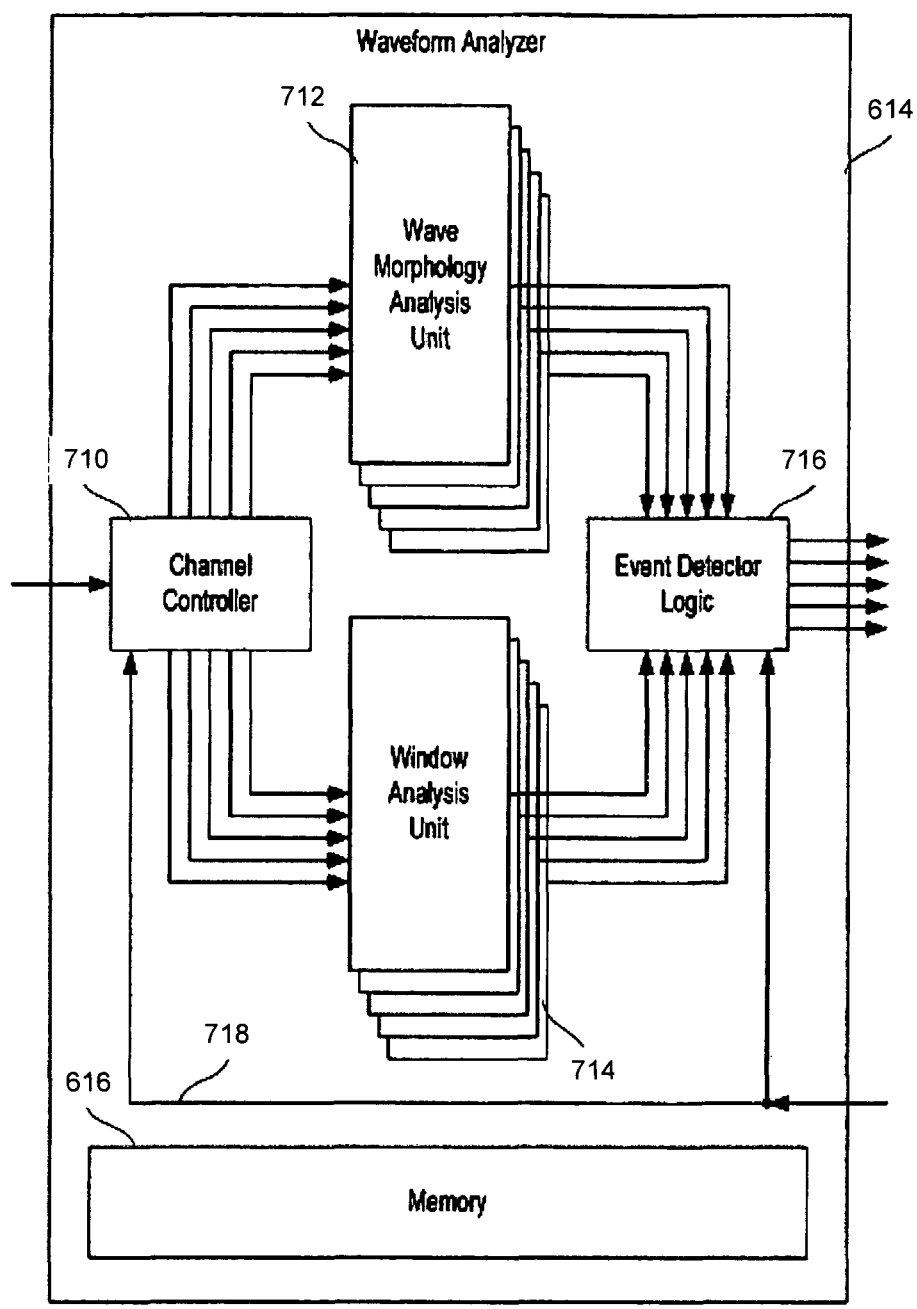
FIG. 7 is a block diagram illustrating components of a waveform analyzer of the detection subsystem of FIG. 6.

In the exemplary waveform analyzer illustrated in FIG. 7, the interleaved digital data stream representing information from all of the active sensing channels is first received by a channel controller 710. The channel controller applies information from the active sensing channels to a number of wave morphology analysis units 712 and window analysis units 714. It is preferred to have as many wave morphology analysis units 712 and window analysis units 714 as possible, consistent with the goals of efficiency, size, and low power consumption necessary for an implantable device. In one embodiment, there are sixteen wave morphology analysis units 712 and eight window analysis units 714, each of which can receive data from any of the sensing channels of the sensing front end 612 (FIG. 6), and each of which can be operated with different and independent parameters, including differing sample rates.

Each of the wave morphology analysis units 712 operates to extract certain feature information from an input waveform. Similarly, each of the window analysis units 714 performs certain data reduction and signal analysis within time windows. Output data from the various wave morphology analysis units 712 and window analysis units 714 are combined via event detector logic 716. The event detector logic 716 and the channel controller 710 are controlled by control commands 718 received from the control interface 618 (FIG. 6).

A "detection channel," as the term is used herein, refers to a data stream including the active sensing front end 612 and the analysis units of the waveform analyzer 614 processing that data stream, in both analog and digital forms. It should be noted that each detection channel can receive data from a single sensing channel; each sensing channel preferably can be applied to the input of any combination of detection channels. The latter selection is accomplished by the channel controller 710. As with the sensing channels, not all detection channels need to be active; certain detection channels can be deactivated to save power or if additional detection processing is deemed unnecessary in certain applications.

In conjunction with the operation of the wave morphology analysis units 712 and the window analysis units 714, a scratchpad memory area 616 is provided for temporary storage of processed data. The scratchpad memory area 616 may be physically part of the memory subsystem 526 (FIG. 5), or alternatively may be provided for the exclusive use of the waveform analyzer 614 (FIG. 6). Other subsystems and components of a neurostimulation device (or system including a neurostimulation device) may also be furnished with local scratchpad memory, if such a configuration is advantageous.

A neurostimulation device may also operate in conjunction with external equipment. For example, in variations in which subject-specific templates (indicative of epileptiform activity or an electrographic seizure) are used, the device may communicate with one or more programming devices configured to receive and analyze brain activity from the device, and receive instructions or detection parameters (e.g., a detection template) to assist in determining epileptiform activity or an electrographic seizure.

Returning now to FIG. 4, a neurostimulation device 200 may be mostly autonomous (particularly when performing its usual sensing, detection, and stimulation capabilities), but may include a selectable part-time wireless link 410 to external equipment such as a programmer 412. The wireless link 410 is established by moving a wand (or other apparatus) having communication capabilities and coupled to the programmer 412 into communication range of the neurostimulation device 200 (for example, an implantable neurostimulation device). The programmer 412 can then be used to manually control the operation of the device, as well as to transmit information to or receive information from the neurostimulation device 200.

The programmer 412 may perform a number of operations. In particular, the programmer 412 may specify and set variable parameters in the implantable neurostimulation device 200 to adapt the function of the device to meet the subject's needs, upload or receive data (including but not limited to stored EEG waveforms, parameters, or logs of actions taken) from the neurostimulation device 200 to the programmer 412, download or transmit program code and other information from the programmer 412 to the neurostimulation device 200, or command the neurostimulation device 200 to perform specific actions or change modes as desired by a physician operating the programmer 412. To facilitate these functions, the programmer 412 may be adapted to receive clinician input 414 and provide clinician output 416; data is transmitted between the programmer 412 and the neurostimulation device 200 over the wireless link 410.

The programmer 412 may be used at a location remote from the neurostimulation device 200 if the wireless link 410 is enabled to transmit data over long distances. For example, the wireless link 410 may be established by a short-distance first link between the neurostimulation device 200 and a transceiver, with the transceiver enabled to relay communications over long distances to a remote programmer 412, either wirelessly (for example, over a wireless computer network) or via a wired communications link (such as a telephonic circuit or a computer network).

The programmer 412 may also be coupled via a communication link 418 to a network 420 such as the Internet. This allows any information uploaded from the neurostimulation device 200, as well as any program code or other information to be downloaded to the neurostimulation device 200, to be stored in a database 422 at one or more data repository locations (which may include various servers and network-connected programmers like the programmer 412). This would allow a subject (and the subject's physician) to have access to important data, including past treatment information and software updates, essentially anywhere in the world where there is a programmer (like the programmer 412) and a network connection. Alternatively, the programmer 412 may be connected to the database 422 over a trans-telephonic link.

In one embodiment, the neurostimulation device 200 is also adapted to receive communications from an initiating device 424, typically controlled by the subject or a caregiver. Accordingly, subject input 426 from the initiating device 424 is transmitted over a wireless link to the neurostimulation device 200; such subject input 426 may be used to cause the neurostimulation device 200 to switch modes (on to off and vice versa, for example) or perform an action (e.g., store a record of EEG data). Preferably, the initiating device 424 is able to communicate with the neurostimulation device 200 through a communication subsystem 530 (FIG. 5), and possibly in the same manner the programmer 412 does. The link may be unidirectional (as with the magnet and GMR sensor described below), allowing commands to be passed in a single direction from the initiating device 424 to the neurostimulation device 200, but in an alternative embodiment of the invention is bi-directional, allowing status and data to be passed back to the initiating device 424. Accordingly, the initiating device 424 may be a programmable PDA or other hand-held computing device, such as a PALM device or POCKETPC. However, a simple form of initiating device 424 may take the form of a permanent magnet, if the communication subsystem 530 (FIG. 5) is adapted to identify magnetic fields and interruptions therein as communication signals.

In an embodiment of the invention, the programmer 412 may be a commercially available PC, laptop computer, or workstation having a CPU, keyboard, mouse and display, and running a standard operating system such as Microsoft WINDOWS, LINUX, UNIX, or APPLE MAC OS. A dedicated programmer apparatus with a custom software package (which may not use a standard operating system) could be developed. The programmer 412 can process, store, play back and display on the display the subject's EEG signals, as previously stored by the neurostimulation device 200 of the neurostimulation device.

The computer workstation software operating program may also have the capability to simulate the detection and prediction of epileptiform activity or an electrographic seizure and other symptoms of patient disorders. Thus, the software operating program of the present invention may allow a clinician to create or modify a subject-specific collection of information comprising algorithms and algorithm parameters for detecting epileptiform activity or an electrographic seizure. The subject-specific collection of detection algorithms and parameters may be referred to herein as a detection template or subject-specific template. The subject-specific template, in conjunction with other information and parameters generally transferred to the implanted device (such as stimulation parameters, time schedules, and other subject-specific information), make up a set of operational parameters for the neurostimulation device.

As mentioned briefly above, epileptiform activity or an electrographic seizure may be detected at any appropriate region of the brain. For example epileptiform activity or an electrographic seizure may be detected by EEG measurements (brain electrical activity measurement) from electrodes implanted in the brain. In particular, epileptiform activity or an electrographic seizure may be detected using electrodes adjacent to a region of the cortex associated with language, such as the primary or associative language cortex. In some variations, epileptiform activity or an electrographic seizure is detected from outside of the brain (e.g., using scalp electrodes).

Language, behavioral, or social dysfunction in persons with an autism spectrum disorder, pervasive developmental delay or acquired epileptic aphasia may be treated by applying neurostimulation in response to the epileptiform activity or an electrographic seizure. The stimulation applied may be related to the epileptiform activity or an electrographic seizure detected. For example, in some variations, the activity (e.g., epileptiform activity or an electrographic seizure) detected from the subject's brain is graded or qualified. For example, the severity or intensity of the epileptiform activity or an electrographic seizure maybe classified, and this classification may be used to determine the neurostimulation applied in response to the epileptiform activity or an electrographic seizure.

C. Applying Neurostimulation to Primary or Associative Language Cortex

After the identification of epileptiform activity (or the onset of epileptiform activity) or electrographic seizure, a cortical language region of the subject's brain is stimulated. Stimulation of primary or associative language cortex in response to epileptiform activity or an electrographic seizure of the brain may improve or protect against language disability. As described above, the same neurostimulation device used to detect epileptiform activity or an electrographic seizure may be used to apply stimulation, or a different neurostimulation device may be used. Any appropriate stimulation may be used. Although the examples described herein involve electrical stimulation, other (or additional) types of stimulation may be used. For example, stimulation may be electrical, chemical, thermal, or the like (or some combination thereof).

As mentioned briefly above, the type and amount of neurostimulation applied may be determined or graded based on the type and/or intensity of epileptiform activity or an electrographic seizure detected. For example, the intensity of neurostimulation may be correlated to the intensity of the epileptiform activity or an electrographic seizure (e.g., prolonged epileptiform activity may trigger prolonged neurostimulation). In some variations, the type of neurostimulation applied may also be regulated. For example, epileptiform activity or an electrographic seizure may trigger predominantly inhibitor neurostimulation of language cortex, or predominantly excitatory neurostimulation of language cortex, or a combination of both. In one variation, stimulation (neurostimulation) is biphasic, charge-balanced pulses of 100 to 200 Hz, 100 to 200 msec duration, pulse width of about 160

μsec, and have a current maximized to tolerability, or begun at a current sufficient to achieve a charge density of 6 μC/cm2 per phase.

A neurostimulator may provide electrical neurostimulation by applying electrical energy to electrodes within or adjacent to language cortex. As mentioned above, a neurostimulation device may include one or more leads, and each lead may have multiple electrodes. Leads and/or electrodes may be adapted to record from and/or apply energy to language cortex. For example, the lead may be a planar electrode having surface electrodes for abutting language cortex. In some variations, leads conform to the shape of language cortex or adjacent regions (e.g., sulci and/or gyri) on the brain surface. Leads may further be adapted to anchor to the correct language cortex area. For example, leads may comprise surface adhesive and/or cortical anchors.

A neurostimulation device may also include one or more subsystems for controlling and applying neurostimulation. For example, the neurostimulation device 200 shown in FIG. 5 includes a therapy subsystem 524 that is capable of applying electrical stimulation (or other therapies) to neurological tissue. Stimulation may be in the form of a substantially continuous stream of pulses, or pulses delivered on a scheduled basis. Thus, therapeutic electrical stimulation may be provided in response to epileptiform events or conditions detected by the waveform analyzer function of the detection subsystem 522. As illustrated in FIG. 5, the therapy subsystem 524 and the EEG analyzer function of the detection subsystem 522 are in communication; this facilitates the ability of therapy subsystem 524 to provide responsive electrical stimulation and/or other therapies, as well as an ability of the detection subsystem 522 to blank the amplifiers while electrical stimulation is being performed to minimize stimulation artifacts. It is contemplated that the parameters of a stimulation signal (e.g., frequency, duration, waveform) provided by the therapy subsystem 524 would be specified by other subsystems in the device 200, and may be specific to the language cortex.

Figure 8:
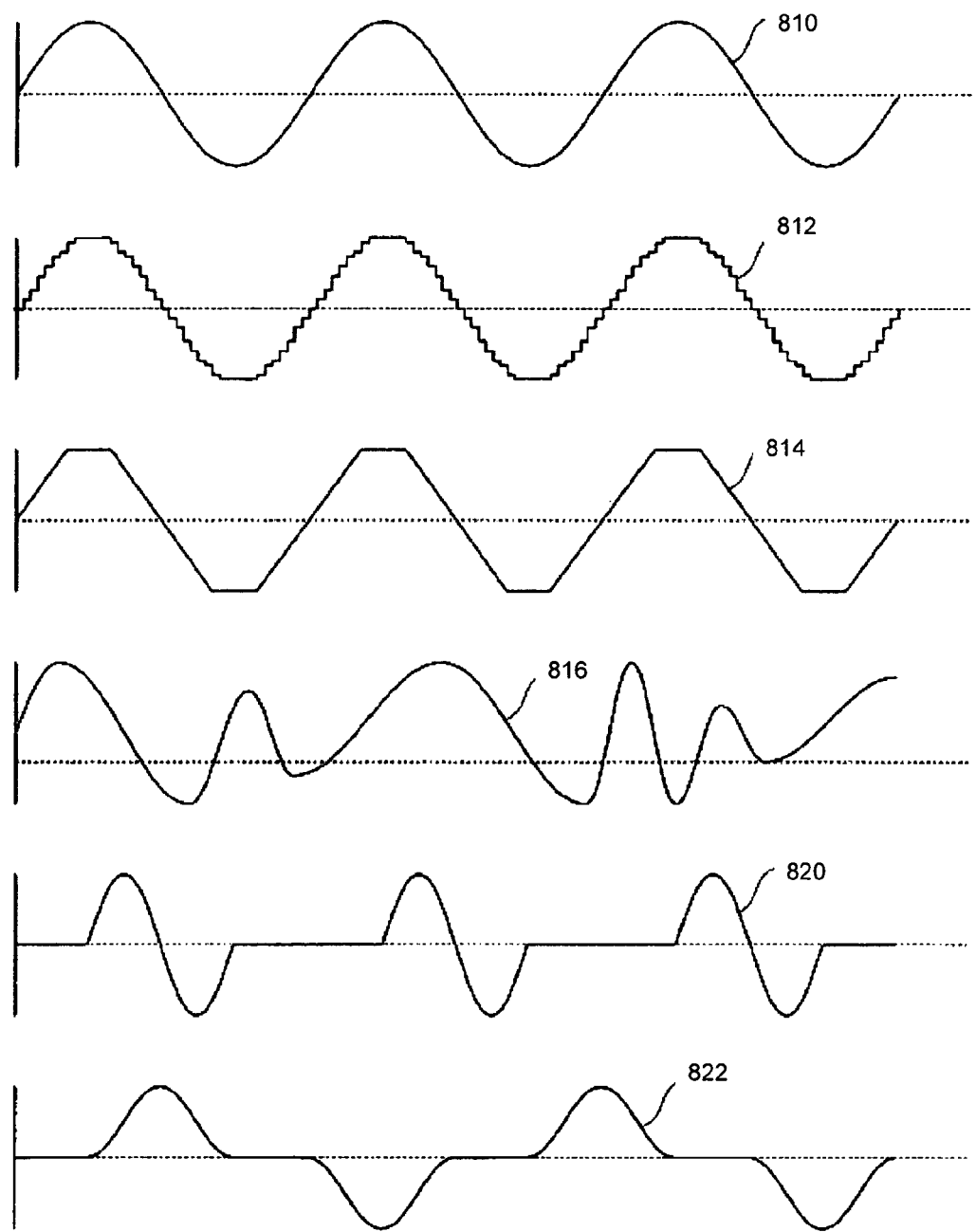
FIG. 8 illustrates exemplary stimulation waveforms, as described herein.

Examples of stimulation waveforms are shown in FIG. 8. In addition to biphasic pulse waveforms, other wave morphologies may have advantageous applications herein. A sinusoidal stimulation signal 810 can be used for scheduled or responsive brain stimulation. In general, sinusoidal and quasi-sinusoidal waveforms may be delivered at low frequencies to have an inhibitory effect, where low frequencies are 0.5 to 10 Hz delivered for 0.05 to 60 minutes at a time. Such waveforms may be applied as a result of determining that inhibition is desired on a scheduled basis, or after conditions indicate that responsive stimulation should be applied. Higher frequency sinusoidal or quasi-sinusoidal waveforms may be used for activation. Amplitudes in the range of 0.1 to 10 mA would typically be used, but attention to safe charge densities is important to avoid neural tissue damage (where a conservative limit is 25 μC/cm$^2$ per phase). It should be noted that the inhibitory and activating functions of various sinusoidal stimulation parameters may vary when applied to different parts of the brain; the above is merely exemplary.

Sinusoidal and quasi-sinusoidal waveforms presented herein may be constructed digitally by the therapy subsystem 524 (FIG. 5) of the neurostimulation device 200. As a result, the sinusoid 810 is really generated as a stepwise approximation, via a series of small steps 812. The time between steps is dependent upon the details of the waveform being generated. It is anticipated that the stair step waveform 812 may be filtered to arrive at a waveform more similar to 814, which would allow for longer periods of time between steps, and for larger steps. Likewise, for the waveforms 816, 820, and 822 (described below), it is assumed that they may be created with a series of steps notwithstanding their continuous appearance in the figures.

A truncated ramp waveform is also possible, where the rate of the ramp, the amplitude reached and the dwell at the extreme are all selectable parameters. The truncated ramp has the advantage of ease of generation while providing the physiological benefits of a sinusoidal or quasi-sinusoidal waveform.

A variable sinusoidal waveform 816 (where the amplitude and frequency are varied while the waveform is applied) is also illustrated. The rate and amplitude of the variation may be varied based upon a predefined plan, or may be the result of the implanted neurostimulation device sensing signals from the brain during application or between applications of the waveform, and adjusting to achieve a particular change in the sensed signals. The variable waveform 816 is illustrated herein as having a positive direct current component, but it should be noted that this waveform, as well as any of the others described herein as suitable for use according to the invention, may or may not be provided with a direct current component as clinically desired.

Waveforms 820 and 822 depict variations where the stimulating waveform is generated having a largely smooth waveform, but having the additional feature where the interval between waveforms is set by varying a selectable delay, as would be used with the traditional biphasic pulse waveforms described previously. In waveform 820, the stimulating waveforms are segments of a sine wave separated in time (of course the same technique could be used for the truncated ramp or other arbitrary morphologies). Waveform 822 shows a variation where the derivative in time of the waveform approaches zero as the amplitude approaches zero. The particular waveform 822 is known as a haversine pulse.

Although the term "haversine pulse" is useful to describe the waveform of 822, it should be noted that all of the waveforms represented in FIG. 8 are considered herein to be generally "non-pulsatile," in contrast with waveforms made up of traditional discontinuous (e.g. square) pulses. As the term is used herein, "non-pulsatile" can also be applied to other continuous, semi-continuous, discontinuous, or stepwise approximated waveforms that are not exclusively defined by monophasic or biphasic square pulses.

In some variations, the default stimulation provided by a neurostimulation device is to stimulate with charge-balanced biphasic pulses. This stimulation may be generated by hardware that automatically generates a symmetric equal-current and equal-duration but opposite-polarity pulse as part of every stimulation pulse; the precise current control enabled by the present invention makes this approach possible. However, the neurostimulation device is preferably programmable to disable the automatic charge balancing pulse, thereby enabling the application of monophasic pulses (of either polarity) and other unbalanced signals.

Alternatively, charge balancing can be accomplished using software by programming the neurostimulation device to specifically generate balancing pulses or signals of opposite phase. Regardless of whether charge balancing is accomplished through hardware or software (or a combination thereof), it is not necessary for each individual pulse or other waveform component to be counteracted by a signal with identical morphology and opposing polarity; symmetric signals are not always necessary. It is also possible, when charge balancing is desired, to continuously or periodically calculate the accumulated charge in each direction and ensure that the running total is at or near zero over a relatively long term and preferably, that it does not exceed a safety threshold even for a short time.

To minimize the risks associated with waveforms that are either unbalanced or that have a direct current component, it is advantageous to use electrodes having enhanced surface areas. This can be achieved by using a high surface area material like platinum black or titanium nitride as part or all of the electrode. Some experimenters have used iridium oxide advantageously for brain stimulation, and it could also be used here (see, e.g., Weiland and Anderson, "Chronic Neural Stimulation with Thin-Film, Iridium Oxide Electrodes," IEEE Transactions on Biomedical Engineering, 47: 911-918 (2000).

Referring back to FIG. 1, in some methods for treating language disorders, a second brain region may also be stimulated 107 in addition to language cortex in response to epileptiform activity or an electrographic seizure. For example, in some variations, detection of epileptiform activity or an electrographic seizure causes the neurostimulation device to stimulate language cortex and also one or more additional cortical regions (e.g., the cingulate cortex) or non-cortical regions of the nervous system. The stimulation applied to the second region may be the same stimulation applied to the language cortex, or it may be different. For example, the stimulus applied to the second region may be excitatory or inhibitory (or a mix of excitatory and inhibitory) independent of the stimulus applied to language cortex. In some variations the stimulus applied to the language cortex and the second region are different modalities (e.g., electrical and thermal or chemical, etc.). In some variations, the timing of the stimulation to the language cortex and the second region are different. For example, the stimulation of the second region may be delayed by some amount of time from the stimulation of language cortex, or may be shorter or longer in duration.

In some variations, the method of treating language, behavior and social disorders (e.g., associated with autism, pervasive developmental disorders and acquired epileptic aphasias) may also include applying neurostimulation to primary and/or associative language cortex and to other regions (such as the cingulated and prefrontal cortex) at scheduled intervals. Thus, neurostimulation is applied at predetermined times or predetermined intervals, even in the absence of detected epileptiform activity or an electrographic seizure. For example, in one variation, the neurostimulation device applies multiple episodes of neurostimulation to language cortex at regular intervals. The time during which such "un-triggered" stimulation is applied may be scheduled, so that it may occur at the same time every day, or in response to the subject's activity. For example, un-triggered stimulation may be scheduled to occur when the subject is sleeping or when the subject is awake. Sleep or arousal may be determined based on a time schedule, based on the subject's brain activity, or based on the subject's metabolic activity. Thus, the stimulus applied to treat a language disorder may depend upon the arousal state of the subject. For example, the intensity and/or duration of a stimulus may be greater or lesser when the subject is sleeping. Since the arousal state of the subject may have effects on the subject's processing and response to language stimulus, it may be beneficial to tailor the response to the subject's arousal state.

In some variations, detection of epileptiform activity or an electrographic seizure initiates the application of a regime of neurostimulation of language cortex. For example, detection of epileptiform activity or an electrographic seizure may trigger a series of stimulation. The series may include stimulation (e.g., excitatory, inhibitory, or a combination) spread out over time. Thus, a stimulus train may be triggered where stimulation is separated by a pre-determined time period (e.g., milliseconds, seconds, minutes, hours, etc.). In some variations a pattern of epileptiform activity or an electrographic seizure may trigger a regime of neurostimulation. For example, two or more episodes of epileptiform activity or an electrographic seizure within a pre-set time period (e.g., milliseconds, seconds, minutes, hours) may trigger application of a series of stimulus waveforms or pulses to the language cortex.

As mentioned briefly above, the neurostimulation device may also be configured to allow the subject or physician to manually apply stimulus to the language cortex. Furthermore, audio, visual, or tactile signals may be provided to the subject to provide feedback from the device. In some variations, the method of treating a subject for a language disorder may include one or more feedback steps, in which the subject or practitioner (e.g., physician, technician, etc.) provides feedback to adjust the stimulation applied to the language region or regions of the subject's brain. The intensity of stimulation applied by the neurostimulation device may be increased or decreased based on the subject's condition.

The methods and systems for treating language disorders described herein may include multiple modalities of therapy such as response stimulation (e.g., stimulation triggered by epileptiform activity or an electrographic seizure) and scheduled stimulation. In general, regular or scheduled therapy may be considered advantageous at certain times, and may be scheduled to operate in parallel with responsive therapy modes. Moreover, the neurostimulation device 200 may also gather data to enable therapy refinement in connection with the programmer 412 (FIG. 4) and other external equipment.

A subject may be treated for a language disorder by applying the treatment methods described herein. A subject in need of treatment of a language disorder may include a subject having autism, pervasive developmental disorders, and/or acquired epileptic aphasias.

An exemplary method for treating a language disorder associated with autism, pervasive developmental disorder or acquired epileptic aphasias may include the step of implanting a device for detecting epileptiform activity or an electrographic seizure. In some variations, a non-responsive (e.g., un-triggered) stimulation is first applied to the subject's language cortex. This therapy may include electrical stimulation as discussed herein. This initial course of therapy may be continued until improvement is observed, or for some predetermined period of time. Following the initial course of therapy, the neurostimulation device may be used to process inputs and monitor brain activity by receiving electrical signals corresponding to the electrical activity of the subject's brain. Electrographic activity may be analyzed. If epileptiform electrographic activity is detected from the observed electrical activity, then an appropriate neurostimulation is applied to language cortex (e.g., the primary or associative language cortical region of a subject's brain). Monitoring may be continuous. For example, after a first epileptiform activity or an electrographic seizure is detected and language cortex is stimulated, the monitoring continues until the device is removed or disabled (e.g., by the subject or medical professional). In some variations the monitoring is not continuous, but can be turned on or off, or scheduled to turn on or off.

While the foregoing detailed description of various embodiments of the present invention are set forth in some detail, the invention is not limited to those details. The methods and systems for treating language, behavioral and/or social disorders according to the invention can differ from the disclosed embodiments in numerous ways. In particular, it will be appreciated that the methods described herein may include one or more additional steps for treating language disorders, including language disorders associated with the autism spectrum disorders, pervasive developmental delay and acquired epileptic aphasias. Furthermore, the methods may be used as part of treatments of disorders encompassing but not limited to language disorders. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries.

What is claimed is:

1. A method of treating a language disorder in a human patient, comprising:
    continuously monitoring with an implanted responsive neurostimulator electrical signals sensed from a first region of the patient's brain related to the language disorder during a selected period when the patient is experiencing a stage of sleep;
    detecting in the continuously monitored electrical signals with the neurostimulator the occurrence of one or more of the following events: epileptiform activity that causes a language disorder, and an electrographic seizure that causes a language disorder;
    responding to the occurrence of the one or more events by applying neurostimulation from the neurostimulator to a second region of the patient's brain for treating the language disorder, wherein the second region is a primary or associative language cortical region; and
    responding to the occurrence of the one or more events by applying neurostimulation from the neurostimulator to a third region of the patient's brain for treating the language disorder, wherein the third region is different from both the first and second region.

2. The method of claim 1, wherein continuously monitoring electrical signals sensed from a first region of the patient's brain further includes continuously monitoring electrical signals sensed by at least one electrode implanted in or adjacent the first region.

3. The method of claim 2, wherein responding to the detection of the one or more events by applying neurostimulation to the second region of the patient's brain further includes delivering stimulation through at least one electrode implanted in or adjacent the second region.

4. The method of claim 1, wherein the first region and the second region are the substantially the same region.

5. The method of claim 1, wherein the third brain region is selected from the group consisting of: the cingulate gyms and a non-cortical region of the nervous system.

6. The method of claim 1, further comprising applying neurostimulation to at least one of the first, second and third regions at a plurality of scheduled intervals during the selected period even in the absence of an occurrence of the one or more events.

* * * * *

UNITED STATES PATENT AND TRADEMARK OFFICE
CERTIFICATE OF CORRECTION

| | | |
|---|---|---|
| PATENT NO. | : 9,162,051 B2 | Page 1 of 1 |
| APPLICATION NO. | : 11/525586 | |
| DATED | : October 20, 2015 | |
| INVENTOR(S) | : Martha J. Morrell | |

It is certified that error appears in the above-identified patent and that said Letters Patent is hereby corrected as shown below:

In the claims, (Column 22, line 21) reads:

5. The method of claim 1, wherein the third brain region is selected from the group consisting of: the cingulate ~~gyms~~ and a non-cortical region of the nervous system.

(Column 22, line 21) should read:

5. The method of claim 1, wherein the third brain region is selected from the group consisting of: the cingulated <u>gyrus</u> and a non-cortical region of the nervous system.

Signed and Sealed this
Sixteenth Day of February, 2016

Michelle K. Lee
*Director of the United States Patent and Trademark Office*